United States Patent [19]
Kurane et al.

[11] Patent Number: 5,804,435
[45] Date of Patent: Sep. 8, 1998

[54] METHOD FOR OBTAINING ORGANIC SOLVENT-RESISTANT MICROORGANISMS AND ORGANIC SOLVENT-RESISTANT MICROORGANISMS OBTAINABLE BY THE METHOD

[75] Inventors: Ryuichiro Kurane, Tsukuba; Takuichi Tsubata, Iruma-gun, both of Japan

[73] Assignees: Tonen Corporation; The Agency of Industrial Science and Technology, both of Tokyo, Japan

[21] Appl. No.: 741,335

[22] Filed: Oct. 29, 1996

Related U.S. Application Data

[63] Continuation of Ser. No. 382,236, Feb. 1, 1995, abandoned.

[30] Foreign Application Priority Data

Feb. 2, 1994 [JP] Japan .................................. 6-011252
Oct. 4, 1994 [JP] Japan .................................. 6-264544

[51] Int. Cl.$^6$ .............................. C02F 3/00; A01N 63/00; C10G 32/00; C12N 1/00
[52] U.S. Cl. .......................... 435/282; 210/600; 210/601; 424/93.47; 435/172.1; 435/252.1; 435/252.34; 435/262.5; 435/264; 435/281; 435/877
[58] Field of Search .................................. 210/600, 601; 435/252.1, 172.1, 262.5, 264, 281, 252.34, 282, 877; 424/93.47

[56] References Cited

U.S. PATENT DOCUMENTS

| | | | |
|---|---|---|---|
| 5,342,778 | 8/1994 | Moriya et al. | 435/252.1 |
| 5,518,726 | 5/1996 | Moriya et al. | 424/282.1 |

FOREIGN PATENT DOCUMENTS 0 218 734 A  4/1987  European Pat. Off. .

OTHER PUBLICATIONS

F. Weber et al., *Microbiology*, 140:2013–2017 (1994).
R. Aono et al., *Agric. Biol. Chem.*, 55(7):1935–1938 (1991).
C. Moss et al., *Appl. Microbiol.*, 24(4):596–598 (1972).
H. Shima et al., *Agric. Biol. Chem.*, 55(4):1197–1199 (1991).
A. Inoue et al., *J. Ferment. Bioeng.*, 71(3):194–196 (1991).
K. Moriya et al., *J. Ferment. Bioeng.*, 76(5):397–399 (1993).
K. Moriya et al., *J. Ferment. Bioeng.*, 76(3):168–173 (1993).
W. Morrison et al., *J. Lipid Research*, 5:600–608 (1964).
C. Laane et al., *Biotechnology and Bioengineering*, 30:81–87 (1987).
A. Inoue et al., *Nature*, 338:264–266 (1989).
Y. Minoda et al., *Agr. Biol. Chem.*, 37(1):45–50 (1973).
K. Yamada et al., *Agr. Biol. Chem.*, 32(7):840–845 (1968).
J. Kilbane, *Tibtech*, 7:97–101 (1989).
K. Malik, *Process Biochemistry*, pp. 10–12 (1978).
J. Gallagher et al., *FEMS Microbiology Letters*, 107:31–36 (1993).
M. van Afferden et al., *Arch Microbiol.*, 153:324–328 (1990).
A. Laborde et al., *Appl. Environ. Microbio.*, 34(6):783–790 (1977).
T. Omori et al., *Appl. Environ. Microbiol.*, 58(3);911–915 (1992).
F. Sagardia et al., *Appl. Microbiol.*, 29(6):722–725 (1975).

*Primary Examiner*—Leon B. Lankford, Jr.
*Assistant Examiner*—Deborah K. Ware
*Attorney, Agent, or Firm*—David G. Conlin; Peter F. Corless; Dike, Bronstein, Roberts & Cushman, LLP

[57] ABSTRACT

The present invention provides a method for obtaining organic solvent resistant microorganisms which comprises subjecting a microbial parent strain to mutagenesis and then to selective cultivation in the presence of 0.1% to 10% by volume (v/v) of concentrations of a toxic organic solvent, and the organic solvent resistant microorganisms obtainable by the method. In addition according to the present invention, a microorganism which is natively hydrophilic and has useful functions but does not show resistance to organic solvents and can not express the useful functions in the organic solvents may be converted into a microorganism capable of growing in the presence of such toxic organic solvents and expressing the useful functions that the hydrophilic parent strain bears natively. Also a bio-desulfurization bacterium mutant capable of decomposing hardly removable organic sulfur compounds under microaerobic conditions in the presence of organic solvents may be obtained by the use of a bacterium belonging to the genus and species *Pseudomonas putida* as the parent strain. Furthermore, the specific strains mutated from the parent strain are *Pseudomonas putida* No. 69-1 (FERM BP-4519), *Pseudomonas putida* No. 69-2 (FERM BP-4520) and *Pseudomonas putida* No. 69-3 (FERM BP-4521).

6 Claims, 5 Drawing Sheets

METHOD FOR OBTAINING ORGANIC SOLVENT-RESISTANT MICROORGANISMS AND ORGANIC SOLVENT-RESISTANT MICROORGANISMS OBTAINABLE BY THE METHOD

This application is a continuation of application(s) Ser. No. 08/382,236 filed on Feb. 1, 1995, now abandoned.

BACKGROUND OF THE INVENTION

1. Field of the Invention

This invention relates to a method for obtaining organic solvent-resistant microorganisms by means of conversion (i.e., mutation and selective cultivation) and to organic solvent-resistant microorganisms obtainable by the method.

It also provides a biological desulfurization method in which an organic solvent-resistant microorganism capable of decomposing organic sulfur compounds is used.

2. Prior Art

Biotechnology including the use of bioreactors has been limelighted and advanced in various industrial field. It includes techniques of biocatalysts such as microorganisms and enzymes which have utilizable functions and activities.

Such biocatalysts can be employed in, for example, production of alcohols, antibiotics, amino acids, proteins, hormones or isomerized sugars, asymmetric resolution of amino acids, environmental clearing, and fuel cells, all of which being used in aqueous systems.

Applications of the biotechnology have also been currently examined in the field of petroleum-related and chemical industries, but no practical applications have yet been achieved in the fields that often employ nonaqueous systems because biocatalysts such as microorganisms can exhibit their activities only in the presence of a large quantity of water thus being hydrophilic whilst they are generally inactivated and therefore cannot survive, grow or react in the presence of a large quantity of oils or organic solvents.

On the other hand, the demand for petroleum in the world is still high due to necessity for the world-wide industrial activation, increase in the consumption in the developing countries, plateauing of the development of oil-substitutive energy sources, and limitation of energy-saving. Especially, demand for gasoline, kerosene and light oil remains strong and the structure of demand for petroleum is rapidly directing toward light-gravity oils.

As the demand for light petroleums increases more and more, the solution or improvement of energy-saving or environmental problems has been called for in the field of petroleum refining. However, since the current refining techniques including distillation and chemical reactions have already reached mature stages, the researchers' concern is now directed toward the application of new techniques including biotechnology to the petroleum refining process.

Examples of the problems to be solved by the application of biotechnology to the petroleum refining process include the conversion of a prior art petroleum refining process which requires operation conditions of high temperature and high pressure into a process by which the refining can be effected at ordinary temperature and at ordinary pressure, as well as the ensured removal of organic sulfur compounds.

In particular, it is a very important object to establish a process for removing organic sulfur compounds from oil by use of microorganisms, in order to cope with the recently arising global environmental problems.

In the administrative side, reducing a sulfur content in light oil or kerosene from the current level of 0.5% to 0.05% after 5 years has now been examined.

Petroleum normally contains 0.05 to 5% of sulfur in the form of not only a sulfur element but also in the form of sulfate; sulfite; thiosulfate; benzothiophene, dibenzothiophene and alkylbenzothiophene which contain a thiophene group; and the like. Of these sulfur compounds, the thiophene backbone-containing dibenzothiophene and alkylbenzothiophene especially pose a problem in the petroleum refining process, because they are difficult to remove by current physicochemical processes for desulfurization.

Known microorganisms capable of performing biodegradation of the organic sulfur compounds which are difficult to be decomposed are those growing in a nitrogen-substituted atmosphere (referred to as "microaerobic" hereinafter) as reported by Makino et al. ("Screening of microorganisms which assimilate sulfur-containing organic compounds in petroleum components", April, 1992, the Agricultural Chemical Society of Japan).

However, since microorganisms have no resistance against organic solvents in general, the biodegradation of organic sulfur compounds by using such microorganisms requires a large quantity of water which entails a disadvantage that the scale of a desulfurization process becomes enormous.

As an attempt to apply microorganisms to organic solvent systems, studies have been conducted on the isolation of organic solvent-resistant bacteria from natural sources (Akira Inoue and Koki Horikoshi, "A Pseudomonas thrives in high concentrations of toluene", Nature, vol.338, p.264–268, Mar. 16, 1989).

However, organic solvent-resistant bacteria do not always have industrially useful functions, and many of them show only the resistance.

The influence as well as technical advance in the industrial field will be great when the above mentioned problems are solved by the development of a method by which microorganisms that are hydrophilic in nature but have many useful functions can be converted efficiently into organic solvent-resistant strains while retaining the useful functions.

In addition, since most of the prior art organic solvent-resistant microorganisms are aerobic, the biodegradation by use of such strains poses a problem that they can hardly be applied to petroleum industry or the like which employ a number of steps that require thin air (oxygen) conditions (i.e., anaerobic conditions and/or microaerobic conditions).

The term "microaerobic conditions" as used herein means conditions in which oxygen is present in a small quantity but at a level of equal to or lower than the explosion limit oxygen content.

In consequence, it can be said that one of problems in various industrial fields such as chemical industries which employ organic solvent systems is to find microorganisms that have functional activities such as resistance to organic solvents and decomposition, synthesis and/or conversion activities upon various reactants of interest under aerobic or microaerobic conditions, although such microorganisms have not yet isolated.

SUMMARY OF THE INVENTION

The present invention provides a method for obtaining an organic solvent-resistant microorganism which comprises subjecting a microbial parent strain to mutagenesis and then to selective cultivation in the presence of an organic solvent.

According to one embodiment of the present invention, at least one of the following variations is observed by the mutagenesis:

(i) A cellular fatty acid composition of the microbial parent strain is varied by the mutagenesis;

(ii) A lipopolysaccharide composition of the microbial parent strain is varied by the mutagenesis;

(iii) A content of trans form unsaturated fatty acids, branched chain fatty acids and/or saturated fatty acids with odd carbon numbers in the cellular fatty acid composition is increased by the mutagenesis;

(iv) The ratio of an intracellular free fatty acid to total fatty acids is increased by the mutagenesis;

(v) Fatty acids with odd carbon numbers are increased in the microbial cells through oxidation of lower straight chain fatty alcohols by the mutagenesis; or (vi) Fatty acids with odd carbon numbers are increased through the contact with a highly toxic organic solvent by the mutagenesis;

(vii) High molecular weight side portions of intracellular lipopolysaccharides are reduced or deleted by the mutagenesis.

The present invention also provides organic solvent-resistant microorganisms obtainable by the above mentioned method. In the micoorganisms, partial or entire properties of their parent strain may be conserved. As such properties the biodegradability of organic sulfur compounds is exemplified. According to one embodiment of the present invention, several *Pseudomonas putida* strains which have the improved biodegradability of organic sulfur compounds are provided.

The present invention further provides a method of the biological desulfurization of organic compounds such as organic sulfur compounds characterized by use of the microorganisms of the present invention (in aerobic and/or microaerobic conditions).

DETAILED DESCRIPTION OF THE INVENTION

In this context, the present inventors have conducted intensive studies with the aim of isolating microorganisms which can be used even in the field of petroleum or chemical industry and found that organic solvent-resistant microorganisms can be obtained by subjecting a corresponding parent microorganism to mutagenesis and subsequent selective cultivation in an organic solvent.

Thus, according to the present invention, there is provided a method for obtaining an organic solvent-resistant microorganism which comprises subjecting a microbial parent strain to mutagenesis and then to selective cultivation in the presence of an organic solvent.

In the present invention, the mutagenesis of a microbial parent strain may be effected by various means such as irradiation with ultraviolet rays, γ-rays or X-rays, and mutagenesis treatment with various mutagens such as nitrosoguanidine and EMS (i.e., ethylmethane sulfonate), but preferably a treatment which can vary a cellular fatty acid composition of the microbial parent strain. When the cellular fatty acid composition is changed, it is preferable to increase trans form unsaturated fatty acids, branched chain fatty acids, or saturated fatty acids with odd carbon numbers in the cellular fatty acid composition of the microorganism, because the increase in the content of these fatty acids results in reduction of lipid fluidity in the membrane of the microorganism. Examples of such fatty acids include, but not limited to, heptadecenoic acid, dodecanoic acid and heptadecanoic acid.

In addition, to afford an organic solvent resistance to a microorganism by mutagenesis, the microbial parent strain is subjected to mutagenesis in such a manner that it acquires at least one of the following properties (see Examples 5 to 7 described later). That is, (a) the ratio of an intracellular free fatty acids to total fatty acids is high;

(b) the high molecular weight portions (O chains or O antigens) of intracellular lipopolysaccharides are sharply reduced or deleted;

(c) fatty acids with odd carbon numbers within the microorganic cells are increased by oxidation of lower straight chain fatty alcohols such as heptanol, nonanol and the like; and (d) intracellular fatty acids with odd carbon numbers are increased by contact with a highly toxic organic solvent.

It can be assumed that the organic solvent resistance is afforded to an organic solvent-resistant microorganism when it acquires the above properties. Although not intended to be restricted by theory, its action mechanism can be thought as follows.

The highly toxic organic solvent means an organic solvent having a small log P value, namely an organic solvent which easily dissolves in water, and it is therefore important for a bacterium to become hydrophobic to exclude such a highly toxic organic solvent. And the free fatty acid is generally a fatty acid which does not contain a glyceryl phosphate, so its hydrophobicity is higher than that of a fatty acid integrated into lipid. An important factor in this connection is not an absolute amount of a free fatty acid but a ratio thereof to total fatty acids. Even if the absolute amount is large, the hydrophobicity will be offset when the fatty acid integrated into lipid becomes large in proportion to the absolute amount of a free fatty acid. In addition, the high molecular weight side portions of lipopolysaccharides are those to which a large number of hydrophilic sugars are linked. The remaining portions which are free from such sugars and are embedded into the membrane have considerably small hydrophilicity. Because of this, it is considered that the deletion of the high molecular weight side portions results in the hydrophobicity.

In the present invention any microorganism may be used as the microbial parent strain, but it is preferable to use a microorganism which is susceptible to organic solvents because the improvement of productivity or reaction rate can be expected by the acquirement of resistance to various oils or organic solvents and because the advantage of conversion into an organic solvent-resistant microorganism becomes more clear. Though not particularly limited, bacterial strains belonging to the genus Pseudomonas can be cited as a typical example.

The present invention also relates to organic solvent-resistant microorganisms obtainable by the above method, and it is preferable that the partial or entire properties of their parent strain are conserved within such organic solvent-resistant microorganisms.

Examples of useful properties (functions) which are inherent to parent strains and are conserved in the organic solvent-resistant microorganisms include, but not limited to, degradation functions, synthetic activities (or functions) such as asymmetric syntheses, and conversion activities or functions. In addition, it is possible to apply the microorganisms of the present invention to various reactions which are advantageous in terms of of yield, efficiency or the like when the reactions are carried out in organic solvent systems.

Examples of the conservation of degradation functions include organic solvent-resistant microbial strains in which an excellent ability to decompose hardly removable organic sulfur compounds is conserved and which have been obtained by the aforementioned method from *Pseudomonas putida* No. 69 (FERM P-13262; deposited on Nov. 6, 1992, at Microorganism Deposition Center, National Institute of Bioscience and Human Technology, Agency of Industrial Science and Technology, the Ministry of Industrial Trade and Industry, Japan; Japanese Patent Application No. 4-350074) as their parent strain which is a hydrophilic bio-desulfurization bacterium capable of decomposing and removing hardly removable organic sulfur compounds. That is, they are *Pseudomonas putida* No. 69-1 (FERM BP-4519), *Pseudomonas putida* No. 69-2 (FERM BP-4520) and *Pseudomonas putida* No. 69-3 (FERM BP-4521) which have been deposited on Dec. 27, 1993, at Microorganism Deposition Center, National Institute of Bioscience and Human Technology, Agency of Industrial Science and Technology, the Ministry of Industrial Trade and Industry, Japan.

These microorganisms are organic solvent-resistant strains capable of performing desulfurization under microaerobic conditions in the presence of organic solvents and are therefore one of preferred embodiments of the present invention. That is to say, the application of these microorganisms to the petroleum refining or coal desulfurization steps will make it possible to establish a more efficient, energy-saving and safe desulfurization process.

In the method of the present invention, the selective cultivation step which is carried out by adding an organic solvent to a microorganism may be effected by spreading a mutagenized organic solvent-susceptible microorganism on an agar plate medium and overlaying thereon an organic solvent at a predetermined concentration ratio or by culturing the mutagenized organic solvent-susceptible microorganism in a liquid medium containing the organic solvent of interest. Also, other conditions such as pH, temperature and aeration rate (when aerated) can be easily set by those skilled in the art, and it is a matter of course that preferred conditions are those under which microorganisms can grow.

The organic solvent used in the present invention may be of any kind, provided that it is an organic solvent against which a microorganism is going to have resistance.

As organic solvents having extremely high toxicity (bactericidal activity) on microorganisms, 1-heptanol and benzene can be exemplified (Akira Inoue and Koki Horikoshi, "Pseudomonas thrives in high concentrations of toluene", Nature, vol.338, p.264–268, Mar. 16, 1989). Therefore, it was substantiated in the Examples of the present invention that organic solvent-resistant microorganisms can be obtained by use of 1-heptanol, 1-nonanol or 1-decanol.

However, since it is evident for those skilled in the art that organic solvent-resistant microorganisms can be obtained by the method of the present invention by use of other organic solvents too, it is to be understood that the organic solvents used herein are not limited to those used in the Examples.

Also, although the degradation function is exemplified in the Examples of the present invention as a useful function inherent to the parent strain, other embodiments making use of the parent strain's other useful functions including for example synthetic activities (functions) such as asymmetric synthesis of esters by lipase or functions to convert long chain hydrocarbons into long chain fatty acids will also be apparent for those skilled in the art and practiced easily.

The following can be exemplified as preferred embodiments of the method of the present invention, but the present invention is not limited thereto.

1. A method for obtaining organic solvent-resistant microorganisms wherein the microbial parent strain is an anaerobic microorganism and/or a microaerobic microorganism.

2. A method for obtaining organic solvent-resistant microorganisms wherein the microbial parent strain is a bacterium belonging to the genus Pseudomonas.

3. A method for obtaining organic solvent-resistant microorganisms wherein the aforementioned bacterium belonging to the genus Pseudomonas is an organic solvent-susceptible microorganism.

4. A method for obtaining organic solvent-resistant microorganisms wherein the aforementioned organic solvent-susceptible microorganism is *Pseudomonas putida* No. 69 (FERM P-13262).

The present invention will be illustrated in more detail by the following non-limited Examples.

EXAMPLES

Reference Example

Firstly, the method for obtaining *Pseudomonas putida* No. 69 is described.

A test tube equipped with a sealable cap was charged with each soil sample collected from various sources, a culture medium A (the following materials are contained per liter: ammonium nitrate 1.0 g, dipotassium hydrogenphosphate 2.0 g, potassium dihydrogenphosphate 1.0 g, yeast extract 30 mg, peptone 30 mg, beef extract 30 mg, magnesium chloride 100 mg, calcium chloride 10 mg, iron chloride (III) 10 mg, manganese chloride 10 mg and zinc chloride 10 mg) and 1000 ppm of dibenzothiophene as a typical example of hardly removable organic sulfur compounds, 99.99% nitrogen gas was thoroughly bubbled into the culture medium and immediately sealed with the cap, and then the tube was shaken at 30° C. to obtain grown bacterial strains. One of these strains was purified, named *Pseudomonas putida* No. 69 and deposited at National Institute of Bioscience and Human Technology, Agency of Industrial Science and Technology, Japan, under the accession number FERM P-13262.

This strain is a bio-desulfurization bacterium which can decompose not only dibenzothiophene but also other hardly removable organic sulfur compounds such as alkyldibenzothiophene and the like.

Example 1

Pseudomonas putida No. 69 was exposed to ultraviolet rays and subjected to selective cultivation in the presence of an organic solvent to obtain bacterial strains capable of decomposing dibenzothiophene, as a typical example of hardly removable organic sulfur compounds, under microaerobic conditions in the presence of the organic solvent.

Firstly, Pseudomonas putida No. 69 was suspended in NB liquid medium manufactured by Bacto (containing 8 g of Nutrient Broth in 1 liter) and shaking-cultured at 30° C. until logarithmic growth phase (turbidity at 660 nm, 0.3 to 0.4), and 1 ml of the resulting culture broth was concentrated and spread on NB agar medium (containing 8 g of Nutrient Broth and 15 g of Bacto-agar).

The agar medium was placed directly below a 15 W bactericidal lamp (UV of 253.7 nm) with a distance of 60 cm and irradiated for 20 to 25 seconds so that the viable ratio of the microorganism became $10^{-3}$ to $10^{-4}$. Immediately thereafter, 1-heptanol was added to a depth of 1 mm, and the resulting plate was covered with aluminium foil and cultured at 30° C. After 2 weeks, colonies grown were purified by repeating subculture three times using NB agar medium on which 1-heptanol was overlaid.

Bacterial strains obtained in this manner were named Pseudomonas putida No. 69-1, Pseudomonas putida No. 69-2 and Pseudomonas putida No. 69-3, which have been deposited on Dec. 27, 1993, at Microorganism Deposition Center, National Institute of Bioscience and Human Technology, Agency of Industrial Science and Technology, the Ministry of Industrial Trade and Industry, under FERM BP-4519 for Pseudomonas putida No. 69-1, FERM BP-4520 for Pseudomonas putida No. 69-2, and FERM BP-4521 for Pseudomonas putida No. 69-3.

Example 2

The strains obtained in Example 1 were tested for the ability to decompose dibenzothiophene under microaerobic conditions in the presence of an organic solvent in the following manner.

Each of Pseudomonas putida No. 69-1, Pseudomonas putida No. 69-2 and Pseudomonas putida No. 69-3 which have been grown on 1-heptanol-overlaid NB agar medium was suspended in 20 ml of culture solution B (containing 0.8 g of Nutrient Broth in 1 liter), 0.2 ml of 1-decanol (or 1-nonanol) was added to the suspension and then the upper layer of the culture was replaced by 99.99% nitrogen gas.

After sealing, shaking culture was carried out for a whole day and night at 30° C. The culture broth was centrifuged to remove the culture solution B, and the thus precipitated cells were suspended in culture solution A and then transferred into a vial containing 20 ml of culture solution A. To this was added 1.05 ml or 2.22 ml of 1-decanol (or 1-nonanol) containing 20 mg of dibenzothiophene, to a final concentration of 5% or 10% (v/v), followed by the replacement of air in the upper layer of the culture by nitrogen gas having the same purity as described in the foregoing and subsequent cultivation at 30° C. with sealing. After 20 days, the medium pH was adjusted to 2.5 with hydrochloric acid, and remaining dibenzothiophene was extracted with 20 ml of ethyl acetate. Quantitative determination was carried out by a gas chromatography. GC 14A (Shimadzu) was used for the gas chromatography, and OV17 1.5% 80/100 mesh Chromosorb WAW DWCS (G L Science) was used as the column. Analysis was carried out under the following conditions. The injector temperature was set to 290° C., the column temperature was raised from 155° C. to 185° C. at a rate of 10° C. per minute, and the detection was effected at 290° C. using FID (Flame Ionization Detector). Carbazole was used as an internal standard. Results of the analyses are shown in Table 1 as mean values of two or more samples. Data in the table represent a concentration (ppm) of decomposed dibenzothiophene.

TABLE 1

| Strain | 5% Decanol | 10% Decanol | 5% Nonanol | 10% Nonanol |
|---|---|---|---|---|
| No. 69-1 | 77.5 | — | 18.5 | 0 |
| No. 69-2 | 68.0 | 38.5 | 24.0 | 6.0 |
| No. 69-3 | 106.0 | 38.5 | 32.5 | 7.0 |

Example 3

Pseudomonas putida No. 69 or Pseudomonas putida No. 69-3 was suspended in a 500 ml conical flask containing 75 ml of NB liquid medium supplemented with 10 mM magnesium sulfate and 5 mM calcium chloride, both in final concentrations, and 75 ml of 1-heptanol and shaking-cultured at 30° C. The turbidity at 660 nm and the number of viable cells were measured at predetermined time intervals.

Figure 1:
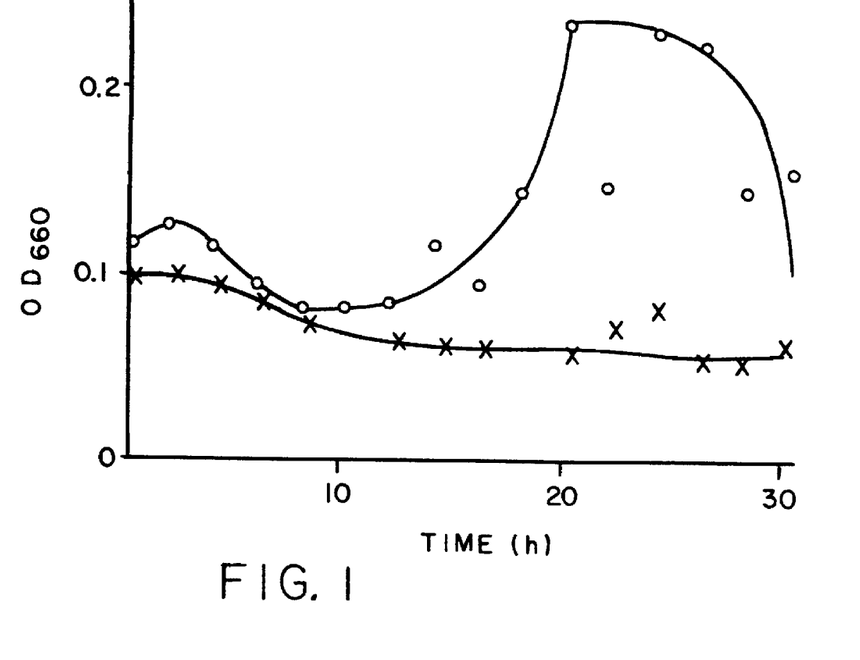
FIG. 1 is a graph showing the change in turbidity at 660 nm on time during cultivation of *Pseudomonas putida* No. 69 (X) or *Pseudomonas putida* No. 69-3 (○) in the presence of 50% (v/v) 1-heptanol.
Figure 2:
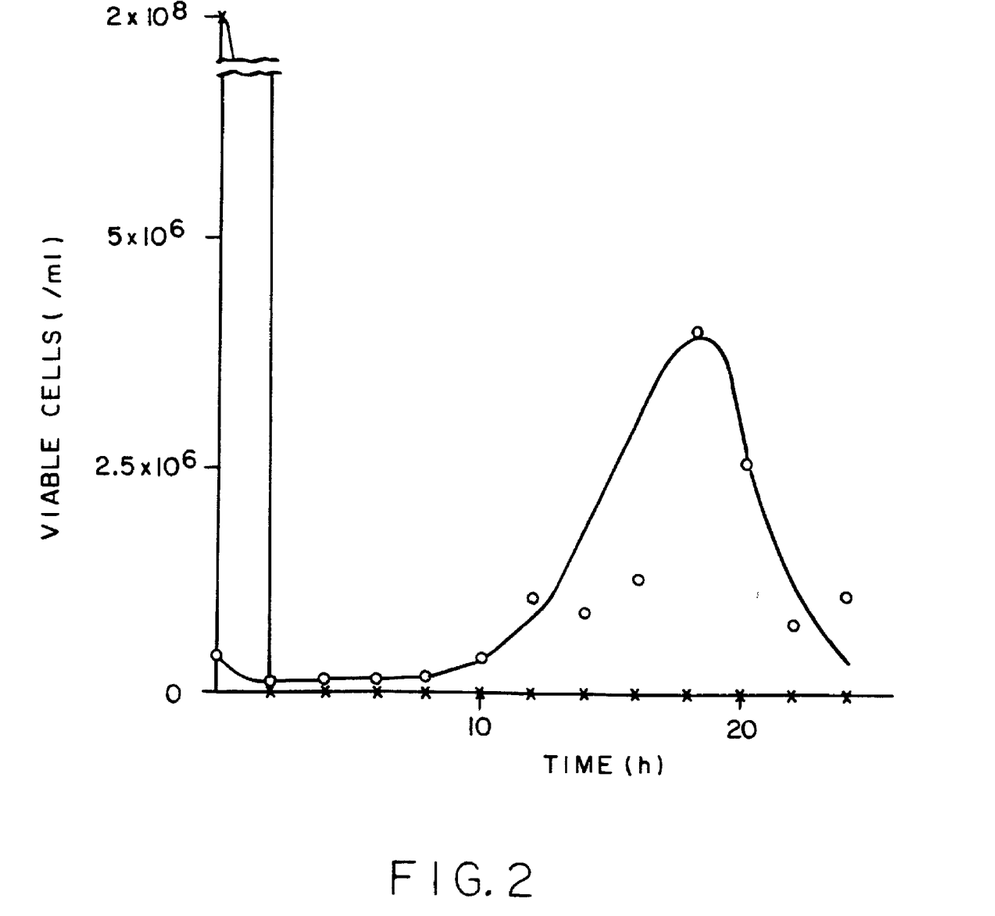
FIG. 2 is a graph showing the number of viable cells of *Pseudomonas putida* No. 69 (X) or *Pseudomonas putida* No. 69-3 (○) when cultured under the same conditions as in FIG. 1.

The number of viable cells was measured as follows. A 0.1 ml portion of the culture broth was mixed with 9.9 ml of 0.9% (w/v) sodium chloride solution to make a 100-fold dilution, and the dilution was further serially diluted to prepare $10^{-3}$, $10^{-4}$, $10^{-5}$, $10^{-6}$, $10^{-7}$ and $10^{-8}$ dilutions. 0.1 ml of each dilution was spread on NB agar medium and cultured at 30° C. for 2 days. Colonies formed were counted to calculate the number of viable cells in 1 ml of the original culture broth. The results are shown in FIGS. 1 and 2.

Example 4

Changes in the fatty acid composition between the obtained organic solvent-resistant microorganism obtained after mutation and the organic solvent-susceptible microorganism before mutation were examined.

Pseudomonas putida No. 69-3 (FERM BP-4521) which has been grown on an agar medium C (containing 15 g of agar per liter of culture solution A) overlaid with 1-heptanol containing 20,000 ppm of dibenzothiophene was suspended in 90% NB liquid medium containing 10% (v/v) 1-heptanol and 10 mM magnesium sulfate and 5 mM calcium chloride and cultured at 30° C. on a shaker for a whole day and night. Cells were collected by centrifugation to extract lipids which were subsequently hydrolyzed into fatty acids to prepare and extract fatty acid methyl esters.

Extraction of lipids was carried out by the method of Bligh and Dyer [E. G. Bligh and W. J. Dyer, Can. J. Biochem. Physiol., vol.37, p.911 (1959)], and hydrolysis of lipids into fatty acids and preparation of fatty acid methyl esters were carried out by the method of Morrison and Smith [W. R. Morrison and L. Smith, J. Lipid Res., vol.5, p.600 (1964)].

The preparation and extraction of fatty acid methyl esters were carried out in the same manner as described above, except that Pseudomonas putida No. 69 (FERM P-13262) was used as an organic solvent-susceptible microorganism and the strain was grown on NB agar medium and then cultured overnight at 30° C. on a shaker in NB liquid medium containing 10 mM magnesium sulfate and 5 mM calcium chloride both in final concentrations.

Figure 3:
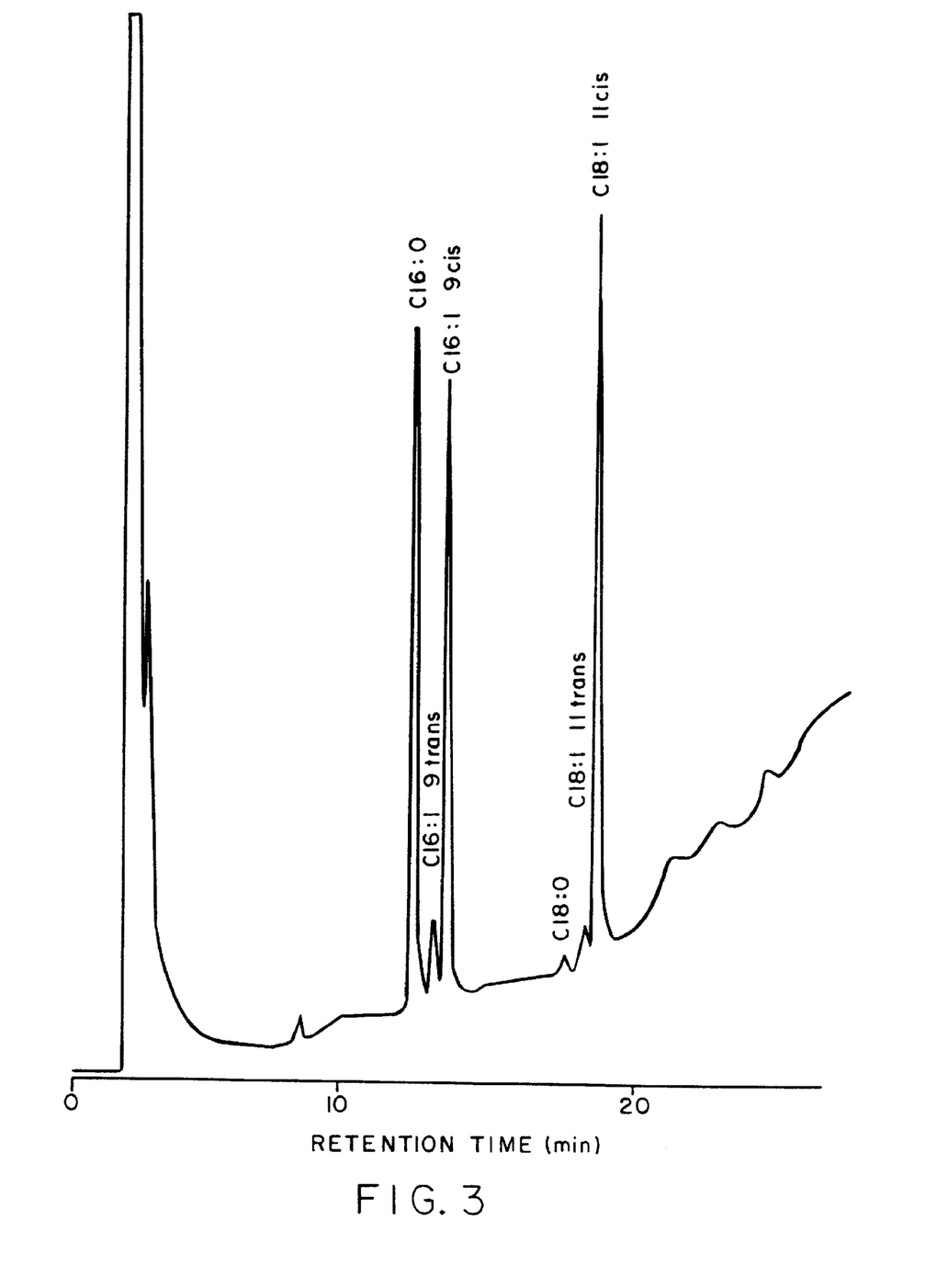
FIG. 3 shows the results of the analysis of fatty acid methyl esters in *Pseudomonas putida* No. 69.
Figure 4:
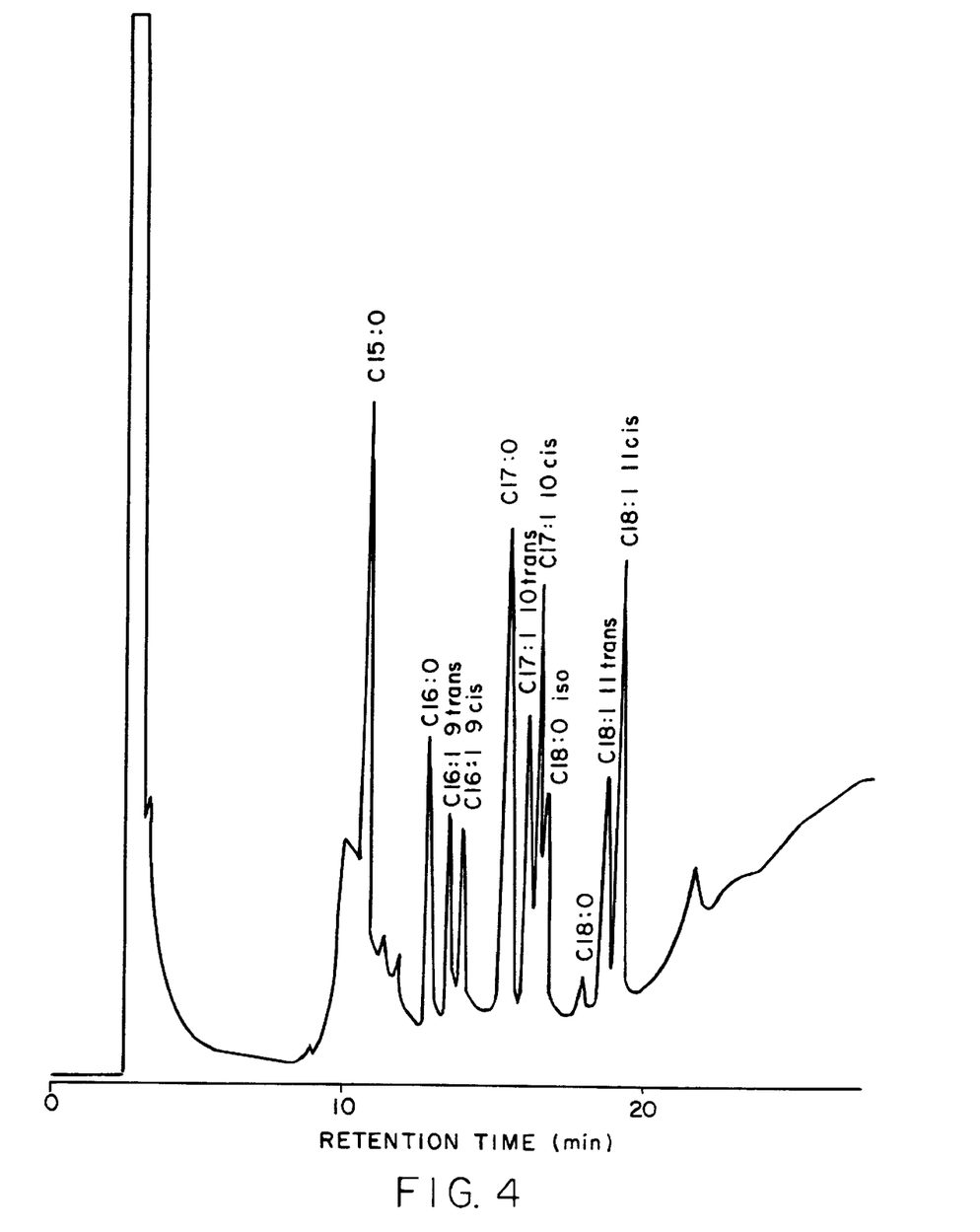
FIG. 4 shows the results of the analysis of fatty acid methyl esters in *Pseudomonas putida* No. 69-3.

Next, conditions for the analysis of the thus extracted fatty acid methyl esters are described. A capillary column manufactured by Shinwa Kako (FFS ULBON HR-SS-10, 0.32 mm in diameter and 50 m in length) was equipped with a gas chromatography analyzer GC 15A (Shimadzu), the injector temperature was set to 250° C., and the column temperature was raised from 150° C. to 220° C. at a rate of 2° C. per minute. Detection was effected by FID at a detector temperature of 250° C. The results are shown in FIGS. 3 and 4.

It is evident from the results that the fatty acid composition of the strain before mutation is typical for *Pseudomonas putida*, while fatty acids having a unsaturated bond(s) or branched chain(s) (for example, C17:1, iso C18, etc) are contained in a large amount or number in the obtained mutated strains.

Example 5

*Pseudomonas putida* No. 69-3 (FERM BP-4521) was cultured at 30° C. for about 1 week on N agar medium (containing 8 g of Nutrient Broth and 15 g of Bacto-agar per liter, and adjusted to 5 mM calcium chloride and 10 mM magnesium sulfate) soaked with n-heptanol, 2-octanone, 2-heptanol, ethoxybenzene, n-octanol or n-nonanol, and a portion of the grown cells were transferred into N liquid medium (containing 8 g of Nutrient Broth per liter, and adjusted to 5 mM calcium chloride and 10 mM magnesium sulfate) containing 10% by volume of the same respective organic solvent and cultured at 30° C. on a shaker. Cells of each experiment were collected when their growth reached stationary phase. A portion of the cells were used for the extraction of total fatty acids by the method of Bligh and Dyer (Bligh, E. G. and W. J. Dyer, *Can. J. Biochem. Physiol.*, vol.37, pp.911–917, 1959) and methylation thereof by the method of Morrison and Smith (Morrison, W. R. and L. Smith, *J. Lipid Res.*, vol.5, pp.600–608, 1964). Also, a portion of the remaining cells were used for the methylation of free fatty acids with 5% hydrochloric acid-methanol solution in accordance with the method of Cohen et al. (Cohen, M., R. G. H. Morgan and A. F. Hoffman, *J. Lipid Res.*, vol.10, pp.614–616, 1969). Detection of fatty acid methyl esters was carried out using Shimadzu GC 15A. FFS ULBON HR-SS-10 capillary column (Shinwa Kako) was used in the analysis, and the column temperature was raised from 40° C. to 220° C. at a rate of 2° C./min. Identification of peaks was effected by using commercially available standards. The results are shown in Tables 2 and 3.

TABLE 2

Quantitative ratio of individual fatty acids derived from *Pseudomonas putida* No. 69-3 cultured in 10% (v/v) of various organic solvents to total fatty acids

| Organic solvent (Log P) | 15:0 | 16:0 | 16:1 trans | 16:1 cis | 17:0 | 17:1 trans | 17:1 cis | iso18 | 18:0 | 18:1 trans | 18:1 cis |
|---|---|---|---|---|---|---|---|---|---|---|---|
| n-Nonal (3.4) | 0.052 | 0.325 | 0.031 | 0.062 | 0.064 | 0.014 | 0.151 | 0.014 | 0.151 | 0.047 | 0.176 |
| n-Octanol (2.9) | n.d | 0.335 | 0.035 | 0.255 | n.d | n.d | n.d | n.d | 0.102 | 0.023 | 0.249 |
| Ethoxy benzene (2.6) | n.d | 0.335 | 0.239 | 0.071 | n.d | n.d | n.d | n.d | 0.024 | 0.241 | 0.090 |
| 2-Heptanol (2.4) | n.d | 0.399 | 0.167 | 0.050 | n.d | n.d | n.d | n.d | 0.117 | 0.207 | 0.060 |
| 2-Octanone (2.4) | 0.061 | 0.297 | 0.142 | 0.059 | 0.047 | 0.027 | 0.013 | 0.008 | 0.050 | 0.164 | 0.133 |
| n-Heptanol (2.4) | 0.233 | 0.058 | 0.066 | 0.037 | 0.109 | 0.122 | 0.137 | 0.072 | 0.025 | 0.039 | 0.049 |

Each of the data shown in the table represents the ratio of a peak area of individual fatty acids to a peak area of total fatty acids in a GC pattern.
The term "n.d" means "not detectable".
(Reference) -- Culture of the parent strain *Pseudomonas putida* No. 69 in organic solvent-free medium: $C_{16}$ 0.312, trans $C_{16}$ 0.015, cis $C_{16}$ 0.317, $C_{18}$ 0.00734, trans $C_{18}$ 0.00614, cis $C_{18}$ 0.343.

TABLE 3

Quantitative ratio of individual free fatty acids derived from *Pseudomonas putida* No. 69-3 cultured in 10% (v/v) of various organic solvents to the total amount of free fatty acids and lipid-incorporated fatty acids

| Organic solvent (Log P) | 15:0 | 16:0 | 16:1 trans | 16:1 cis | 17:0 | 17:1 trans | 17:1 cis | iso18 | 18:0 | 18:1 trans | 18:1 cis |
|---|---|---|---|---|---|---|---|---|---|---|---|
| n-Nonal (3.4) | 0.117 | 0.059 | 0.090 | 0.101 | 0.114 | 0.136 | 0.107 | 0.101 | 0.023 | 0.054 | 0.078 |
| n-Octanol (2.9) | n.d | 0.078 | 0.362 | 0.093 | n.d | n.d | n.d | n.d | 0.029 | 0.316 | 0.153 |

TABLE 3-continued

Quantitative ratio of individual free fatty acids
derived from *Pseudomonas putida* No. 69-3 cultured in 10% (v/v)
of various organic solvents to the total amount of free fatty
acids and lipid-incorporated fatty acids

| Organic solvent (Log P) | Fatty acids | | | | | | | | | | |
|---|---|---|---|---|---|---|---|---|---|---|---|
| | 15:0 | 16:0 | 16:1 trans | 16:1 cis | 17:0 | 17:1 trans | 17:1 cis | iso18 | 18:0 | 18:1 trans | 18:1 cis |
| Ethoxy benzene (2.6) | n.d | 0.267 | 0.305 | 0.216 | n.d | n.d | n.d | n.d | 0.075 | 0.280 | 0.201 |
| 2-Heptanol (2.4) | n.d | 0.299 | 0.408 | 0.402 | n.d | n.d | n.d | n.d | 0.040 | 0.383 | 0.399 |
| 2-Octanone (2.4) | 0.490 | 0.640 | 1.054 | 0.361 | 0.586 | 0.705 | 0.641 | 0.814 | 0.128 | 0.525 | 0.463 |
| n-Heptanol (2.4) | 0.685 | 0.616 | 0.629 | 0.629 | 0.788 | 0.786 | 0.788 | 0.763 | 0.235 | 0.802 | 0.640 |

Each of the data shown in the table represents the ratio of a peak area of individual fatty acids to a total peak area of free fatty acids and lipid-incorporated fatty acids in a GC pattern.
The term "n.d." means "not detectable".

Table 2 shows the ratio of each intracellular fatty acid to total fatty acids detected after culturing in each organic solvent, revealing that intracellular trans form fatty acids and fatty acids with odd carbon numbers have especially high ratios. Also, Table 3 shows that the ratio of a free fatty acid to total fatty acids increases, with especially high ratios of trans form fatty acids and fatty acids with odd carbon numbers.

Example 6

Figure 5:
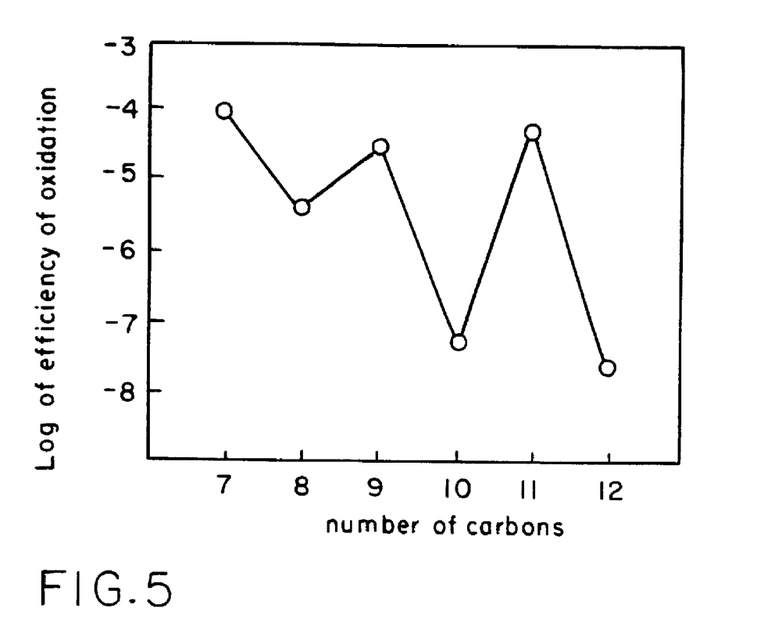
FIG. 5 shows the comparison of oxidation efficiencies of straight chain fatty alcohols having different carbon numbers into corresponding fatty acids.

After culturing under the same culture conditions as described in Example 5 (except for the use of n-heptanol, n-octanol, n-nonanol, n-decanol, n-undecanol and n-dodecanol), the culture supernatant was obtained by centrifugation (10,000 g, 10 minutes). Acids were extracted from the supernatant with 5% sodium bicarbonate, acidified to pH 1 with hydrochloric acid and then extracted with ether. After complete evaporation to dryness by a rotary evaporator, methylation was carried out by the aforementioned method of Morrison and Smith. Detection of fatty acid methyl esters was carried out in the same manner as described in Example 5. The results are shown in FIG. 5 (abscissa: carbon numbers of fatty alcohol, ordinate: common logarithm of conversion efficiency).

As seen from the drawing, straight chain fatty alcohols with odd carbon numbers are oxidized with higher efficiency into corresponding fatty acids with odd carbon numbers.

Example 7

After culturing under the same culture conditions as described in Example 5 (except for the use of 0%, 0.1%, 1.0% and 10.0% by volume of concentrations in experiments for the examination of heptanol concentration dependency of lipopolysaccharides and the use of decalin, n-dodecanol, n-undecanol, n-decanol, n-nonanol, n-octanol, ethoxybenzene and n-heptanol in experiments for the examination of organic solvent dependency), the obtained cells were subjected to proteolysis by the method of Preston and Penner (Preston, M. A. and J. L. Penner, *Infect. Immun.*, vol.55, pp.1806–1812, 1987) and then to electrophoresis by the method of Laemmli and Favre (Laemmli, U. K. and M. Favre, *J. Mol. Biol.*, vol.80, pp.575–599, 1973), followed by the detection of lipopolysaccharides in accordance with the method of Tsai and Frasch (Tsai, C. M. and C. E. Frasch, *Anal. Biochem.*, vol.119, pp.115–119, 1982). The results are shown in FIGS. 6 and 7.

Figure 6:
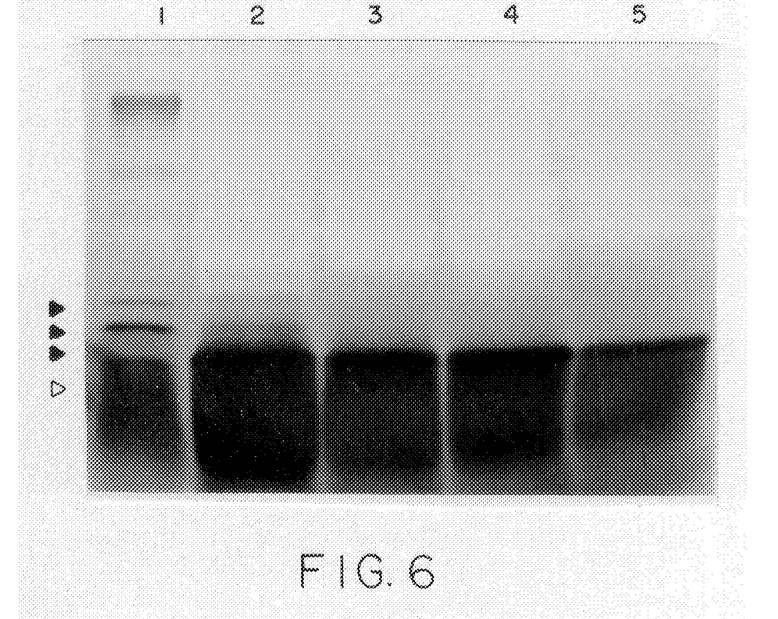
FIG. 6 is an electrophoretic photograph showing n-heptanol concentration dependency of lipopolysaccharide in which lane 1 represents No. 69 (FERM P-13262) cultured as control in N liquid medium not containing any organic solvent, lane 2 represents 0% n-heptanol, lane 3 represents 0.1%, lane 4 represents 1.0%, and lane 5 represents 10%.
Figure 7:
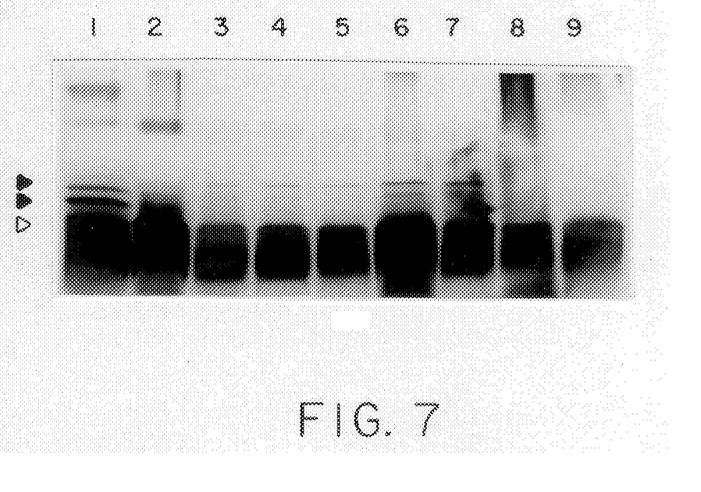
FIG. 7 is an electrophoretic photograph showing organic solvent dependency of lipopolysaccharide in which lane 1 represents No. 69 (FERM P-13262) cultured as control in N liquid medium not containing any organic solvent, lane 2 represents decalin, lane 3 represents n-dodecanol, lane 4 represents n-undecanol, lane 5 represents n-decanol, lane 6 represents n-nonanol, lane 7 represents n-octanol, lane 8 represents ethoxybenzene, and lane 9 represents heptanol.

FIG. 6 shows n-heptanol concentration dependency of lipopolysaccharides, revealing that the high molecular weight side portions have been already deleted even at a heptanol concentration of 0.1%, and the high molecular weight side portions are regenerated in the absence of the organic solvent, as observed in the parent strain. Also, FIG. 7 shows organic solvent dependency of lipopolysaccharides in which organic solvents having a smaller log P are used as the lane No. becomes larger, as seen from analysis of lipopolysaccharides after cultivation in the presence of respective organic solvents. In consequence, it is apparent that the high molecular weight side portions are deleted gradually.

The present invention has the following advantages.

Microorganisms which are capable of growing in organic solvents and expressing useful functions that its hydrophilic parent strain bears inherently could be obtained effectively from a natively hydrophilic microorganism through its mutation or variation. In addition, several biodesulfurization bacteria which are capable of decomposing hardly removable organic sulfur compounds under microaerobic conditions in the presence of organic solvents could be obtained by the use of a bacterium belonging to the genus Pseudomonas as the parent strain.

What is claimed is:

1. A method for obtaining an organic solvent-resistant microorganism, which comprises:

treating a parent microorganism belonging to the genus and species *Pseudomonas putida* with UV irradiation or mutagen;

culturing the treated microorganism in the presence of at least about 0.1% (v/v) to about 10% (v/v) of a toxic organic solvent;

selecting a microorganism having, relative to the parent microorganism, 1) a decrease in high molecular lipopolysaccharides and, 2) at least one change in fatty acids selected from the group consisting of (i) increase in fatty acids with odd carbon numbers through oxidation of lower straight-chained fatty alcohols, (ii) increase in branched fatty acids, (iii) increase in trans unsaturated fatty acids, (iv) decrease in cis unsaturated fatty acids, and (v) increase in the ratio of free fatty acids to total fatty acids; and recovering the selected microorganism.

2. The method of claim 1, wherein the organic solvent-resistant microorganism is *Pseudomonas putida* No. 69-1 (FERM BP-4519), *Pseudomonas putida* No. 69-2 (FERM BP-4520), or *Pseudomonss putida* No. 69-3 (FERM BP-4521).

3. A method for the treatment of a sulfur-containing organic compound which comprises adding a microorganism selected from the group consisting of *Pseudomonas putida* No. 69-1 (FERM BP-4519), *Pseudomonas putida* No. 69-2 (FERM BP-4520), and *Pseudomonas putida* No. 69-3 (FERM BP-4521) to a sulfur-containing organic compound and whereby the sulfur-containing organic compound is degraded.

4. The method of claim 3 wherein the sulfur-containing compound is dissolved in an organic solvent.

5. The method of claim 3, wherein the microorganism is added to the sulfur-containing compound under aerobic conditions.

6. A biologically pure microorganism selected from the group consisting of *Pseudomonas putida* No. 69-1 (FERM BP-4519), *Pseudomonas putida* No. 69-2 (FERM BP-4520), and *Pseudomonas putida* No. 69-3 (FERM BP-4521).

* * * * *

UNITED STATES PATENT AND TRADEMARK OFFICE

CERTIFICATE OF CORRECTION

PATENT NO.: 5,804,435

DATED: September 8, 1998

INVENTOR(S): Kurane et al.

It is certified that error appears in the above-identified patent and that said Letters Patent is hereby corrected as shown below:

On the Cover page, column 1, please delete "[73] Assignees: Tonen Corporation, The Agency of Industrial Science and Technology both of Tokyo, Japan" and insert --[73] Assignees: The Agency of Industrial Science and Technology, Tokyo, Japan--.

Signed and Sealed this

Twenty-eighth Day of September, 1999

Attest:

Q. TODD DICKINSON

*Attesting Officer*    *Acting Commissioner of Patents and Trademarks*